United States Patent [19]

Eichenbaum et al.

[11] 4,377,897
[45] Mar. 29, 1983

[54] OPHTHALMIC NEEDLE AND METHOD FOR MANUFACTURING THE SAME

[75] Inventors: Daniel M. Eichenbaum, Chappaqua, N.Y.; Gerald Martin, North Miami Beach, Fla.; Paul Rehkopf, Murrysville, Pa.

[73] Assignee: Ocular Associates, Hollywood, Fla.

[21] Appl. No.: 289,899

[22] Filed: Aug. 4, 1981

[51] Int. Cl.³ .................. B23P 11/00; B23P 19/04; A61M 1/00
[52] U.S. Cl. .................. 29/516; 29/455 R; 128/276
[58] Field of Search .......... 29/516, 455 R; 128/240, 128/276, 305

[56] References Cited

U.S. PATENT DOCUMENTS

| | | | |
|---|---|---|---|
| 3,085,573 | 4/1963 | Meyer et al. | 128/240 |
| 3,532,476 | 10/1970 | Peehs et al. | 29/516 |
| 3,819,150 | 6/1974 | Kajrup | 29/516 |
| 3,929,126 | 12/1975 | Corsaut | 128/240 |
| 3,986,240 | 10/1976 | Skinner | 29/455 R |
| 3,994,297 | 11/1976 | Kopf | 128/276 |
| 4,037,599 | 7/1977 | Raulerson | 128/214.4 |
| 4,041,947 | 8/1977 | Weiss et al. | 128/276 |
| 4,069,814 | 1/1978 | Clemens | 128/240 |
| 4,114,625 | 9/1978 | Onat | 128/348 |
| 4,299,221 | 11/1981 | Phillips et al. | 128/276 |

*Primary Examiner*—Lowell A. Larson
*Assistant Examiner*—Steven E. Nichols
*Attorney, Agent, or Firm*—Richard M. Saccocio

[57] ABSTRACT

An improved ophthalmic needle and method for manufacturing the same for use with an ophthalmic instrument for extracapsular removal of a cataract. The needle comprises a coaxial tube portion, a separated tube portion, and a tank portion, interposed therebetween for flow conversion purposes. A metal-to-metal seal is effectuated between tubes at the coaxial portion by a spinning method employing a forming die in conjunction with a lathe. A unique use of fixtures is employed to properly orient the various tubes with respect to the tank and to effectuate joint sealing.

3 Claims, 9 Drawing Figures

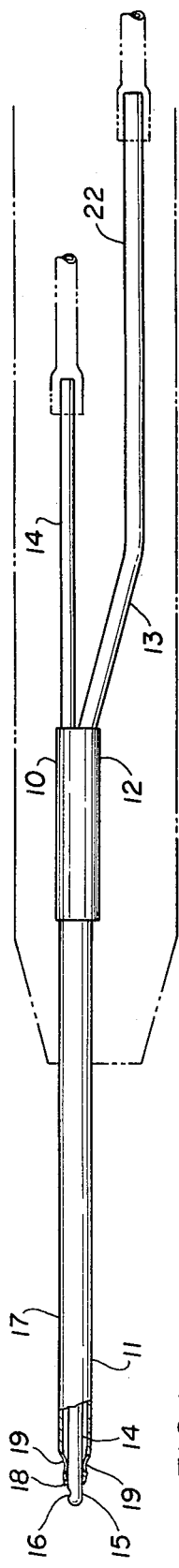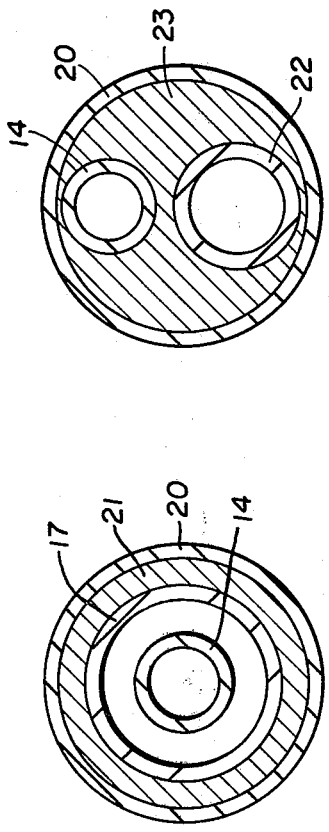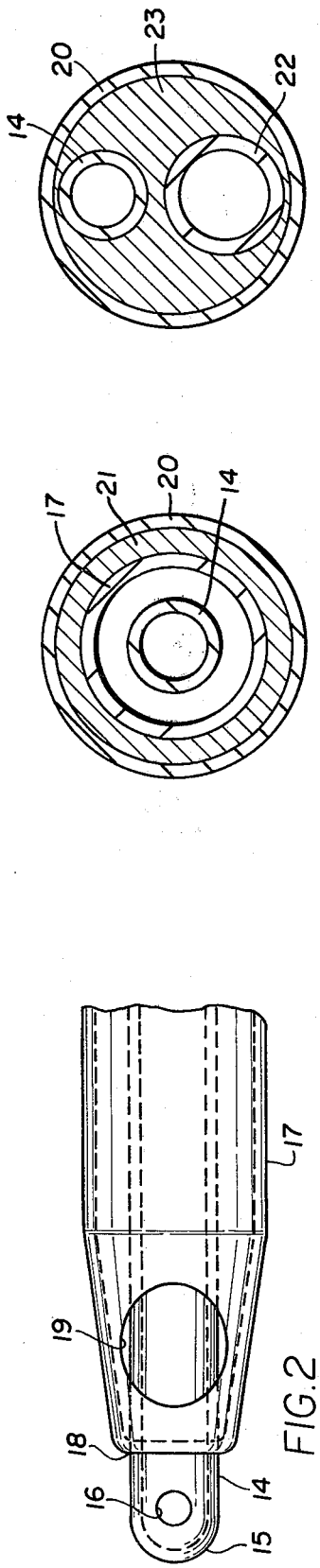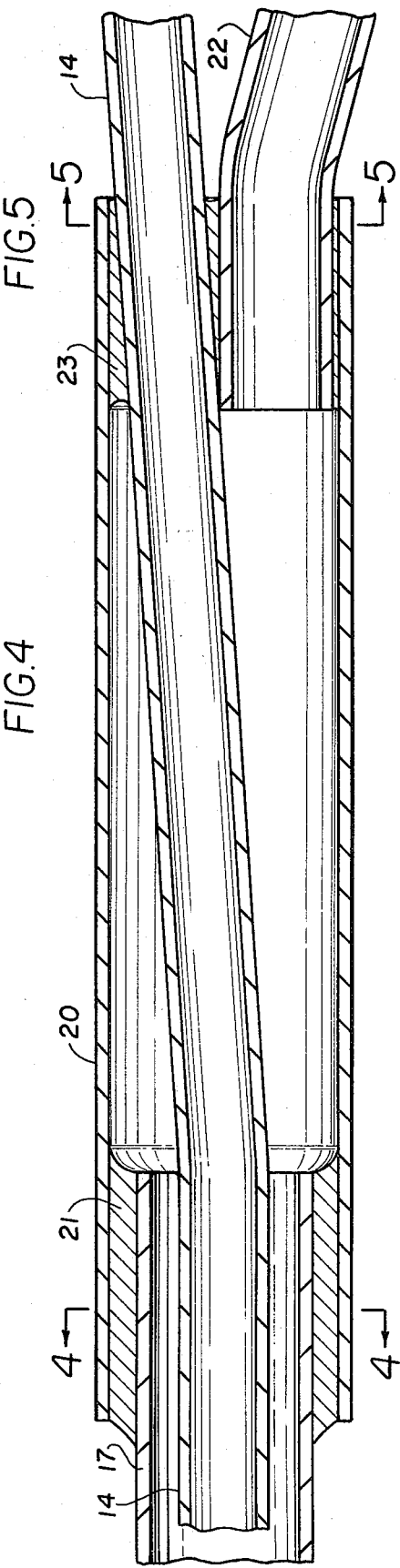

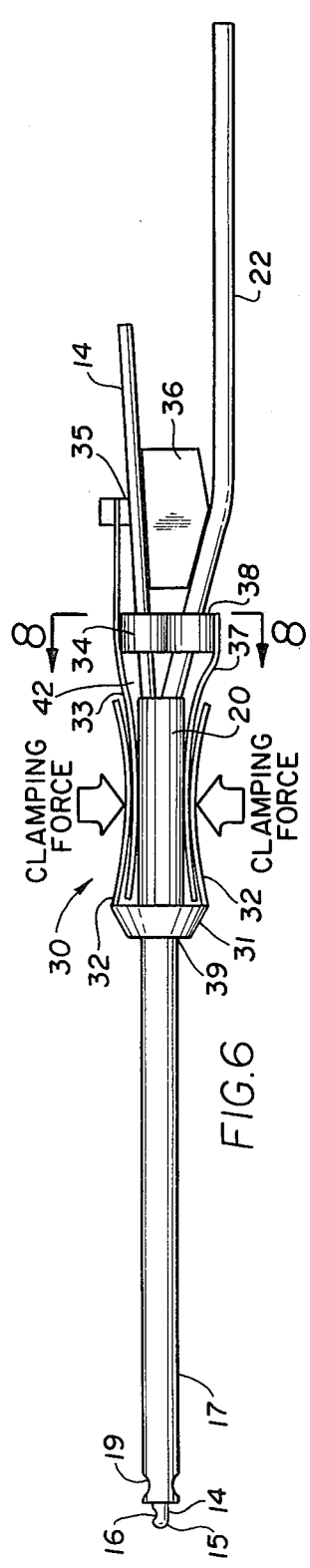
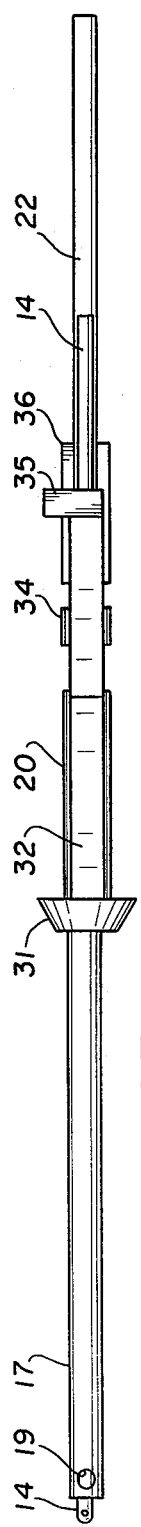
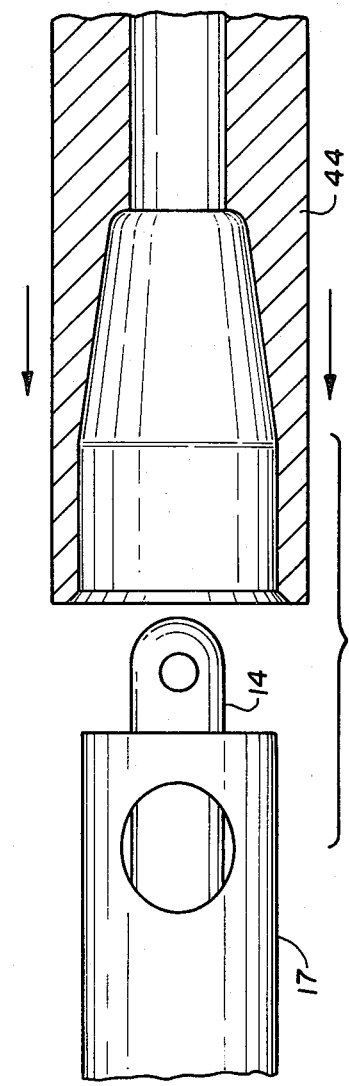
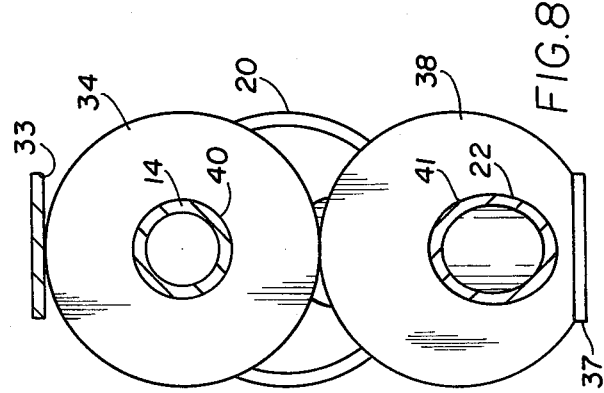

OPHTHALMIC NEEDLE AND METHOD FOR MANUFACTURING THE SAME

BACKGROUND OF THE INVENTION

1. Field of the Invention

This invention relates in general to the field of surgical apparatus for removal of cataracts from an eye and in particular to needle apparatus for use with an ophthalmic instrument for removing cataracts.

2. Description of the Prior Art

In general, there are two surgical techniques for removing cataracts from an eye. Surgical removal of cataracts in today's technology may be broadly classified as intracapsular removal and extracapsular removal. With intracapsular removal, the lens and its outer covering, the lens capsule, are both removed. With extracapsular removal, the anterior portion of the lens capsule is opened and then the cataract is removed. The subject matter of the apparatus disclosed and claimed herein applies to the extracapsular method of removal of cataracts.

With the extracapsular method, soft cataracts or the cortex of hard cataracts are removed by aspiration flow through a needle which is inserted in the eye through the sclera. Irrigation flow of an appropriate fluid is simultaneously provided in order to replenish the aqueous fluid aspirated during the surgery and to maintain the normal round shape of the eye during surgery.

Most prior art ophthalmic instruments used in intraocular surgery employ an abrasive technique or a cutting technique to remove the hard portion of cataracts. Hence, the needles associated with these instruments, although using both irrigation and aspiration flow, include means for abrading or cutting the cataracts. Accordingly, such needles do not exactly constitute prior art, but they do give some general insight to the prior problems and their solutions in the general field of intraocular surgery. One such instrument is shown in U.S. Pat. No. 3,994,297, issued Nov. 30, 1976, Ophthalmic Instrument, by J. David Kopf. The needle involved therein comprises an inner tube which reciprocates in an outer tube causing shearing of intraocular tissue which is then aspirated through the inner tube. The outer tube infuses a saline solution back into the eye. Another ultrasonically vibrated needle is disclosed in U.S. Pat. No. 4,041,947, issued Aug. 16, 1977, by Weiss, et al. The inner tube of the needle aspirates the emulsified hard portion of the cataract while an outer tube provides irrigation fluid.

A prior art needle which is relatively well known is illustrated in pending patent application Ser. No. 084,180, filed Oct. 12, 1979, by Daniel M. Eichenbaum, M.D., Disposable Device to be Utilized in Extracapsular Cataract Surgery, and comprises a double-barreled cannular needle. The instrument disclosed therein is for removal of the soft portion of the cataract by the extracapsular technique.

A type of "needle" in another art, but somewhat similar in concept to the apparatus herein, is disclosed in U.S. Pat. No. 4,037,599, issued July 26, 1977, by James D. Raulerson. Said "needle", however, actually comprises a catheter device used in catherization of a blood vessel during hemodialysis and is used to accomplish the delivery of blood to and from a blood vessel as used in hemodialysis treatment.

Notwithstanding the existence of prior art and presently commercial devices, there is still a need for improved irrigation-aspiration flow apparatus to be used with an ophthalmic instrument for extracapsular removal of cataracts.

SUMMARY OF THE INVENTION

The present invention comprises an improved irrigation-aspiration needle assembly and a method for manufacturing the same for use with an ophthalmic instrument for extracapsular removal of a cataract. The needle assembly includes an inner tube essentially coaxially arranged with an outer tube, a pair of essentially side-by-side parallel arranged connector tubes and a tank interposed between said coaxial tubes and said connector tubes. The inner tube passes through the tank and forms one of the connector tubes extending therefrom. The outer tube and the second connector tube terminate within the tank but at opposite ends thereof. The tank provides flow communication between the outer tube and the second connector tube. At its coaxial portion, the inner tube extends a small distance past the outer tube. A small opening or port is provided in the side of the inner tube within the portion that extends past the outer tube. The outer tube is sealingly connected to the outer diameter of the inner tube by a unique swaging technique and forms a tapered transition portion between the tip of the inner tube and the main body of the outer tube. At least two oppositely disposed ports are provided in the tapered transition portion of the outer tube, with one of the ports being axially aligned with the port in the inner tube.

The needle assembly is uniquely manufactured with the use of a soldering and tube positioning fixture. The fixture positions the various tube members of the needle assembly and securely holds them in position while sealing of the joints is accomplished. The fixture includes heat sink means which prevents the sealing means from forming internal flow obstructions. In other words, it prevents the sealing medium from being internally deposited in areas which would adversely affect irrigation and aspiration flow. The fixture also correctly positions the irrigation and the aspiration tubes relative to the tank at the interface of the connector tubes and the tank. A forming die is used to shape and seal the coaxial portion of the needle assembly.

BRIEF DESCRIPTION OF THE DRAWINGS

For a more complete understanding of the invention, reference is had to the following description taken in conjunction with the accompanying drawings, in which:

FIG. 1 is a front plan view of the needle assembly of the present invention;

FIG. 2 is a side plan view of the tip of the needle in FIG. 1;

FIG. 3 is a partial cross-sectional detailed view of the tank and the tube connections thereto;

FIG. 4 is a cross-sectional view along the line 4—4 of FIG. 1;

FIG. 5 is a cross-sectional view along the line 5—5 of FIG. 1;

FIG. 6 is a plan view of the needle assembly positioned within a fixture used to manufacture the needle assembly;

FIG. 7 is a top view of the needle assembly and the fixture of FIG. 6;

FIG. 8 is a view taken along the line 8—8 of FIG. 6; and,

FIG. 9 is a cross-sectional view of a forming die used to shape and seal the outer tube of the needle assembly.

DESCRIPTION OF THE PREFERRED EMBODIMENTS

Referring now to FIG. 1 of the drawings, the improved needle assembly of the inventive apparatus is shown therein and generally designated by the numeral 10. The ophthalmic instrument which needle assembly 10 is adapted to be used with is partially shown in phantom in the figure. Also shown in phantom are the flexible tubes which are connected to the needle assembly within the ophthalmic instrument. Needle assembly 10 comprises a coaxial portion 11, a tank portion 12, and a side-by-side substantially parallel connector tube portion 13.

Inner tube 14 extends in one piece from the coaxial portion 11, through the tank portion 12, to the substantially parallel connector tube portion 13 which is hereinafter referred to as the connector tube portion. Inner tube 14 comprises a hollow tube closed at one end. Closed end 15 is rounded and includes no sharp ends or surfaces. An opening or aspiration aperture 16 is provided in the side wall of inner tube 14 in close proximity to the rounded end and is in flow communication with the inner diameter of inner tube 14.

An outer tube 17 is essentially coaxially positioned with respect to inner tube 14 and arranged to provide a flow path coaxial with the inner diameter of inner tube 14. The tip portion of outer tube 17 is gently tapered to a point where it meets with inner tube 14 at location 18. Hence, the rounded end 15 and a small portion of inner tube 14 extends axially from location 18. It is to be noted that aspiration aperture 16 is within the portion of inner tube 14 which extends from location 18. The fit up between inner tube 14 and outer tube 17 at location 18 is such that an essentially leakproof joint results without the aid of any additional sealing material. Such leakproof joint obtains from the method of manufacturing the needle assembly 10 which is more fully described hereinafter. A pair of oppositely disposed irrigation apertures 19 are provided in the tapered portion of outer tube 17. Irrigation apertures 19 are in flow communication with the inner diameter of outer tube 17. One irrigation aperture 19 is substantially aligned with aspiration aperture 16 along the lineal centerline of inner tube 14 (see FIG. 2); the other irrigation aperture 19 is located 180° therefrom. Such alignment provides irrigation flow in the immediate vicinity of the cataract aspiration. In this manner, the operating surgeon can visually verify that irrigation flow is being provided during aspiration of the cataract.

As can be seen in FIG. 2, irrigation aperture 19 is not circular. The shape of aperture 19 approximates that of an ellipse or a slightly elongated slot having rounded ends. Such shape maximizes the rate of irrigation flow while also maximizes the circumferential web thickness of outer tube 17 between aperture 19.

The tank portion 19 of needle assembly 10 is depicted in FIGS. 3, 4, and 5. Tank portion 12 comprises a tank 20 which consists of a short section of a hollow tube. Tank portion 12 interfaces with coaxial portion 11 and parallel tube portion 13 and serves to convert the spaced essentially parallel flow through connector tube portion 13 into coaxial flow of fluid through coaxial portion 11. These figures also show a preferred method of sealing between the various tube members to effectuate the above-described flow conversion. At the junction of the coaxial portion 11 and tank portion 12, the outer tube 17 is concentrically arranged relative to and extends within tank 20. An annulus is thereby formed as shown in FIG. 4 which annulus is sealed by solder 21 containing a high percentage of tin and a small percentage of antimony. The soldered joint 21 also functions to structurally connect the free end of outer tube 17 to tank 20.

The junction of tank portion 12 and connector tube portion 13 is depicted in cross section in FIG. 5. As can be seen, aspiration tube 14 and irrigation tube 22 are substantially equally spaced along the vertical cross-sectional centerline of tank 20. Such spacing allows for proper sealing by solder 23 which is composed of the same ingredients as solder 21. The spacing of tubes 14 and 22 is accomplished by the curved shapes given to said tubes as shown in FIG. 3. Irrigation tube 22 is preformed prior to soldering while aspiration tube 14 is so shaped by a fixture during the soldering process which will be more fully explained hereinafter.

In order to manufacture the needle assembly 10, a new and novel method is employed which is hereinafter explained.

Tubes for the tank 20, aspiration tube 14, connector irrigation tube 22, and outer tube 17 are cut to size from appropriate tube stock. The tip 15 of tube 14 may be formed by a spinning process using an appropriately shaped forming die. Holes 16 and 19 are machined in tubes 17 and 14, respectively. Irrigation inlet tube 22 is bent to the shape shown in FIG. 3. The above-stated components are now ready to be assembled and structurally joined together.

An appropriate fixture is used to position the various components in preparation for soldering. A fixture 30 such as that shown in FIGS. 6, 7, and 8 may be used for this purpose. Fixture 30 may comprise three separate subassemblies. A first subassembly may comprise a nosepiece 31 and flexible straps 32 attached thereto; a second subassembly may comprise a flexible strap 33, spacer 34, bar 35, and block 36; a third subassembly may comprise a flexible strap 37 and spacer 38. Clamping forces are applied as shown in FIG. 5 to firmly connect the three aforementioned subassemblies and to firmly hold fixture 30 to needle assembly 10. Straps 32, 33, and 37 are initially straight before the clamping forces are applied.

Tank 20 is heated such as by a soldering iron and solder is applied at location 39 which effectuates the soldered connection between tank 20 and outer tube 17.

Spacers 37 and 38 in conjunction with block 36 may be used to properly position tubes 14 and 22 prior to being soldered to tank 20. Spacers 34 and 38 each contain a hole 40 and 41, respectively, which receive tubes 14 and 22. Application of the clamping forces in conjunction with spacers 34 and 38 and block 36 causes tube 14 to bend away from the axial centerline of tank 20 and creates room for tube 22 to fit within tank 20 as shown in FIG. 5. Tube 14 also assumes the position shown in FIG. 5. Such positioning assures the flow of solder around tubes 14 and 22 and around the inner diameter of tank 20 so as to result in a structurally sound, leakproof joint.

It is to be noted that spacers 34 and 38 are axially displaced a small distance 42 from the end of tank 20. When soldering tubes 14 and 22 to tank 20, heat is applied to tank 20 such as by a soldering gun, while solder is applied within distance 42. When the proper temperature is achieved, the solder will flow within tank 20 and around tubes 14 and 22. Because of the clamping forces applied to straps 32, 33, and 37 which contact tank 20, a heat sink is created which prevents the melting of the solder at joint 39 while the tank 20 is being soldered to tubes 14 and 22. The heat sink also prevents the solder from going too far within tank 20, thereby avoiding any interference with the irrigation and aspiration flow channels within needle assembly 10. Once the solder has solidified, fixture 30 may be removed from needle assembly 10. The three piece construction of fixture 30 permits such removal.

The remaining operation necessary to complete the manufacture of needle assembly 10 consists of forming the tapered portion of outer tube 17 and to make the substantially leakproof joint at location 18. This is accomplished by use of a forming die 44 which has internally machined therein the final shape of the tapered portion of outer tube 17. Needle assembly 10 is appropriately chucked in a machine capable of rotating needle assembly 10. While needle assembly 10 is being rotated, the forming die 44 is gradually brought into contact with needle assembly 10 which gradually forms the tapered portion on outer tube 17 and the leakproof joint at location 18.

When needle assembly 10 is attached to a housing of an appropriate ophthalmic instrument, it is ready for use by a surgeon. The coaxial tip is inserted in an eye through the sclera. The cataract is drawn into the aspiration port 16 as a result of the aspiration flow through inner tube 14. During such aspiration, irrigation flow (in a direction reverse to that of the aspiration flow) enters tube 22, flows through tank 20, and enters outer tube 17. Once in outer tube 17, the irrigation flow and the aspiration flow are coaxial. The irrigation flow simultaneously exits through both irrigation ports 19. Because one of the aspiration ports 19 is axially aligned with irrigation port 16 as shown in FIG. 2, the operating surgeon can continuously verify the existence of the irrigation flow. An undetected interruption of irrigation flow can result in an unsuccessful operation. The present invention, therefore, maximizes the probability of success.

While the invention has been described, disclosed, illustrated and shown in certain terms or embodiments or modifications which it has assumed in practice, the scope of the invention is not intended to be nor should it be deemed to be limited thereby and such other modifications or embodiments as may be suggested by the teachings herein are particularly reserved especially as they fall within the breadth and scope of the claims here appended.

We claim:

1. A method manufacturing an ophthalmic needle having a first portion comprising a first tube positioned within and extending from a second tube, a second portion having side-by-side tubes with one of said tubes being an extension of said first tube and the other being a third tube, and a third portion comprising a fourth tube interposed between said first and said second portions, said fourth tube having a first end which is located at a first end of said second tube and having a second end having said first tube extending therethrough and is located at a first end of said third tube, including the steps of:
   (a) sealing said first end of said second tube to said first end of said fourth tube;
   (b) bending said first tube away from the axial centerline of said fourth tube thereby creating a space between said first tube and the first end of said third tube, and approximately equal spaces between the inner diameter of said fourth tube and the outer diameter of said first tube and between the inner diameter of said fourth tube and the outer diameter of said third tube, at the second end of said fourth tube;
   (c) sealing said first tube, said third tube and said fourth tube at the second end thereof.

2. The method of claim 1 including the step of sealing said first, second, and third tubes to said fourth tube by soldering.

3. The method of claim 2 including the step of sealing the second end of said second tube to said first tube extending therefrom by swagging the second end of said second tube down onto said first tube forming a metal-to-metal seal.

* * * * *